(12) United States Patent
Niu et al.

(10) Patent No.: US 8,383,794 B2
(45) Date of Patent: Feb. 26, 2013

(54) CONFORMATION-SELECTIVE NUCLEIC ACID INHIBITORS OF AMPA GLUTAMATE RECEPTORS

(76) Inventors: Li Niu, Loudonville, NY (US); Zhen Huang, Latham, NY (US)

( * ) Notice: Subject to any disclaimer, the term of this patent is extended or adjusted under 35 U.S.C. 154(b) by 36 days.

(21) Appl. No.: 12/900,636

(22) Filed: Oct. 8, 2010

(65) Prior Publication Data

US 2012/0088818 A1    Apr. 12, 2012

(51) Int. Cl.
*A61K 48/00* (2006.01)
*C07H 21/02* (2006.01)
(52) U.S. Cl. .................................. 536/23.1; 514/44 R
(58) Field of Classification Search ........................ None
See application file for complete search history.

*Primary Examiner* — John Ulm
(74) *Attorney, Agent, or Firm* — Heslin Rothenberg Farley & Mesiti P.C.

(57) ABSTRACT

The present invention relates to novel nucleic acid ligands or aptamers that demonstrate potent and selective inhibition of the open-channel conformation of the α-amino-3-hydroxy-5-methyl-4-isoxazole propionate (AMPA) subtype of ionotropic glutamate receptors.

18 Claims, 10 Drawing Sheets

```
              1         10        20        30        40       50  Copies  A/A(I)
SEQ ID NO: 1  AG1407: AGAUUGUGAAGCGUAGGCUCGAGUUUGUCCCGCGAGCCAAAGAUUCCAGA   17   1.5 ± 0.2
SEQ ID NO: 2  AG1417: UUGAGUUGGAUGCCUGCGCUUAACUGCGCGACUUAUCCAGAGGUAUACGU   10   1.1 ± 0.1
SEQ ID NO: 3  AG1408: UACGCUGACCUUACCCCACAAAAGGGGACCACGCCAACGUAAGCGACAGA    6   1.1 ± 0.1
SEQ ID NO: 4  AG1404: CCCAGACACGGCAGUAAAGAGAAGACUUCCAGAAAAAAGGGGCAACCAGG    6   1.2 ± 0.2
SEQ ID NO: 5  AG1439: AGAAGCAAGCGGGCACGUUACUUAUGUAACUAUACGUGUAGUGCGUUCGG    3   0.8 ± 0.1
SEQ ID NO: 6  AG1230: ACAACCCGCGGAGCACGAGUGAUGCUUCAAAGGCUCCCACCAAAGCAGA     3   1.0 ± 0.0
SEQ ID NO: 7  AG1436: UUCGGCGAUGGUUACGAUGGAAUAGUCGUAACUGUUCCAAAAGCGACAGA    2   1.4 ± 0.2
```

SEQ ID NO: 8    5'GGGAGAAUUCAACUGCCAUCUAGGC( $N_{50}$ )AGUACUACAAGCUUCUGGACUCGGU 3'

Constant Region                    Constant Region

FIGURE 1

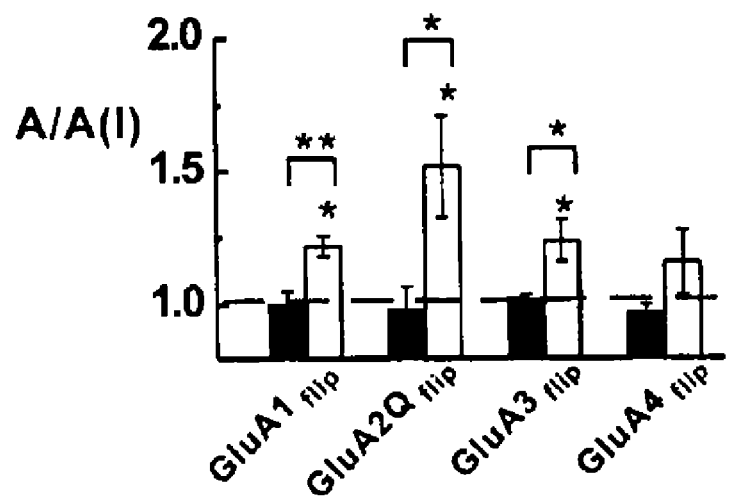
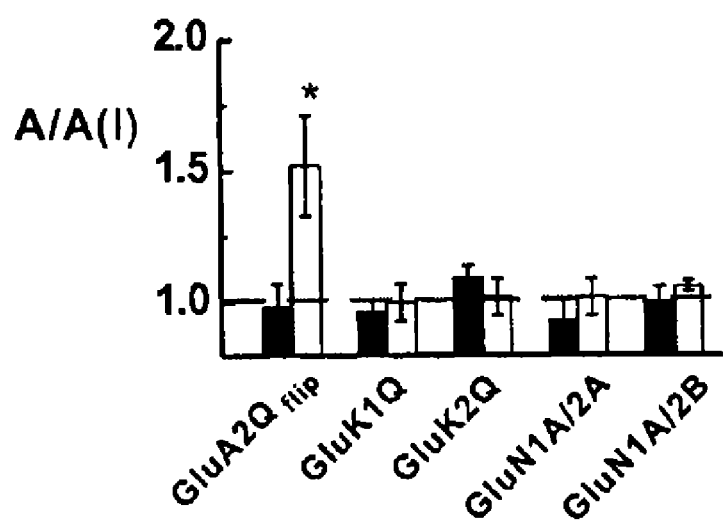
FIGURE 4

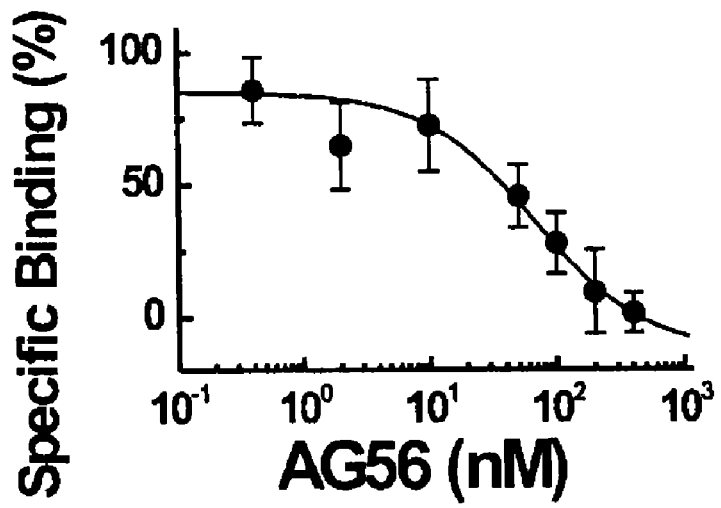
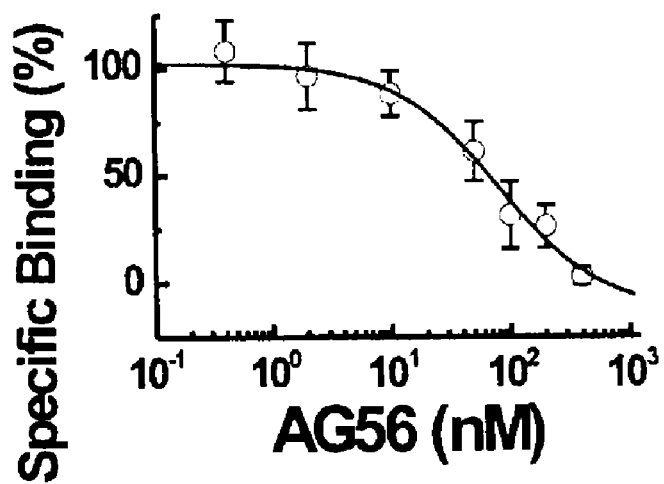
FIGURE 6

| | NUCLEOTIDE SEQUENCE | Designation | # nt |
|---|---|---|---|
| 1 | AGAUUGUGAA GCGUAGGCUC GAGUUUGUCC CGCGAGCCAA AGAUUCCAGA | AG50 | 50 |
| 9 | GAGAUUGUGAA GCGUAGGCUC GAGUUUGUCC CGCGAGCCAA AGAUUCCAGAC | AG52 | 52 |
| 10 | GG AGAUUGUGAA GCGUAGGCUC GAGUUUGUCC CGCGAGCCAA AGAUUCCAGACC | AG54 | 54 |
| 11 | GGGGAGAUUGUGAA GCGUAGGCUC GAGUUUGUCC CGCGAGCCAA AGAUUCCAGACCC | AG56 | 56 |
| 12 | GGGGAGAUUGUGAA GCGUAGGCUC GAGUUUGUCC CGCGAGCCAA AGAUUCCAGACCCC | AG58 | 58 |
| 13 | GGGGGAGAUUGUGAA GCGUAGGCUC GAGUUUGUCC CGCGAGCCAA AGAUUCCAGACCCCC | AG60 | 60 |
| 14 | GGGAGAAUUC AACUGCCAUC UAGGCAGAUU GUGAAGCGUA GGCUCGAGUU UGUCCCGCGA GCCAAAGAUU CCAGA AGUAC UACAAGCUUC UGGACUCGGU | AG1407 | 100 |

FIGURE 10

CONFORMATION-SELECTIVE NUCLEIC ACID INHIBITORS OF AMPA GLUTAMATE RECEPTORS

STATEMENT OF RIGHTS UNDER FEDERALLY-SPONSORED RESEARCH

This invention was made with government support under grant W81XWH-04-1-0106 awarded by the U.S. Department of Defense. The government has certain rights in the invention.

TECHNICAL FIELD

The invention relates to nucleic acid ligands, for example, RNA ligands that bind to α-amino-3-hydroxy-5-methyl-4-isoxazole propionic acid (AMPA)-subtype glutamate ion channel receptors and inhibit the activity of these receptors. More particularly, the nucleic acid ligands of the invention selectively bind to the open-channel conformation of the AMPA glutamate receptor.

BACKGROUND OF THE INVENTION

Ion channel glutamate receptors are ligand-gated transmembrane proteins that can be activated by the binding of glutamate, the principal excitatory neurotransmitter in the brain. Ionotropic glutamate receptors (iGluRs) are, therefore, the major excitatory neurotransmitter receptor proteins in the mammalian brain. As such, these receptors play special roles in brain activities, such as memory and learning, and have been implicated in a variety of neurological diseases, such as post-stroke cellular lesion and amyotrophic lateral sclerosis [Dingledine et al., 1999; Heath and Shaw 2002].

When glutamate, released from a presynaptic neuron, binds to a postsynaptic glutamate receptor, the receptor rapidly changes its conformation and transiently forms an open ion channel, thus resulting in a change of the postsynaptic membrane potential. A postsynaptic potential of sufficient strength triggers an action potential, which will in turn propagate the initial nerve impulse. The major function of iGluRs is to mediate fast synaptic neurotransmission underlying the basic activities of the brain, such as memory and learning. Excessive activation of ionotropic glutamate receptors, particularly the α-amino-3-hydroxy-5-methyl-4-isoxazole-propionate (AMPA) subtype, is known to induce calcium-dependent excitotoxicity. Excitotoxicity has been considered as a general pathogenic mechanism underlying a number of neurological disorders such as amyotrophic lateral sclerosis (ALS), stroke, Alzheimer's disease and Parkinson's syndrome.

Using inhibitors to dampen the excessive activity of these receptors may serve as a treatment for neurological disorders such as ALS or Huntington's disease. To date, Riluzole, an inhibitor of presynaptic glutamate release, is the only drug that benefits the survival of ALS patients. Currently, the majority of AMPA receptor inhibitors are those synthesized by organic chemistry, and many of them show cross activity to kainate receptors, another subtype of iGluRs. The cross activity is not desirable, because the AMPA and kainate receptors have functional differences. Furthermore, the majority of AMPA receptor inhibitors have poor water solubility. In addition, there is a lack of an assay of inhibitor-receptor interactions within the microsecond (μs) to millisecond (ms) time domain. This is because an AMPA receptor opens its channel in the μs time scale and desensitizes within a few ms in the continued presence of glutamate. Consequently, the potency of all AMPA receptor inhibitors has been determined only with the desensitized receptors. These deficiencies have significantly hampered drug development.

Because proteins are generally dynamic and adapt a specific conformation for function, using molecular agents that bind selectively to a specific protein conformation among its conformational repertoire is thus a powerful means to exert a tighter molecular recognition to more effectively regulate the existing function of that protein, and to even engineer a new protein function. For instance, small chemical compounds have been found to stabilize a conformation for some apoptotic procaspases to induce autoproteolytic activation of these proenzymes. Catalytic antibodies have been created, based on transition-state structural analogs, to accelerate chemical reactions by stabilizing their rate-determining transition states along reaction pathways. Developing inhibitors to control excessive receptor activity has been a long pursued therapeutic strategy for a potential treatment of these neurological disorders and diseases.

What is needed, therefore, is an AMPA glutamate receptor inhibitor that is characterized by a high affinity for its target, preferably in the nanomolar range, specificity targeting the glutamate receptor, excellent water solubility and relevance of its inhibitory properties to the functional forms of the receptor rather than the desensitized receptor forms.

SUMMARY OF THE INVENTION

The present invention provides a class of water-soluble high affinity compounds, specifically nucleic acid ligands or aptamers that inhibit glutamate receptor function. In particular, the novel nucleic acid ligands or aptamers of the present invention selectively target the open-channel conformation of AMPA-subtype glutamate ion channel receptor proteins. The open-channel conformation of AMPA receptors exists in the time span of μs to a few ms after glutamate, the endogenous neurotransmitter, binds to the receptor, but before these glutamate-bound receptors turn into the desensitized, closed-channel receptor form.

In one aspect, therefore, the invention relates to novel nucleic acid ligands to AMPA receptors. The nucleic acid ligands or aptamers of the invention are selected by an in vitro iterative process of selection, partitioning and amplification referred to as SELEX. Additionally, the nucleotides of the aptamer may be chemically modified either prior to or after selection of the aptamers by SELEX. In one embodiment, the nucleic acid of the invention is an RNA. Examples of glutamate inhibitors of the invention are nucleic acids that have a nucleotide sequence comprising a nucleotide sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 10, SEQ ID NO: 11, SEQ ID NO: 12, SEQ ID NO: 13, and SEQ ID NO: 14.

In a related aspect, the present invention relates to a method of identifying a nucleic acid ligand that can inhibit glutamate receptor function, specifically by binding to and inhibiting the open-channel conformation of the receptor, the method comprising the steps of: using a saturating concentration of receptor agonist, such as glutamate, to titrate the receptor population to maximize the fraction of receptors in the open-channel conformation; screening a nucleic acid library for a nucleic acid that binds to the open-channel conformation of a glutamate receptor; providing a cell that has been transfected to overexpress the receptor; exposing the cell to glutamate in the presence and absence of the nucleic acid identified by the screening method and measuring the glutamate-induced whole-cell current using laser pulse photolysis of caged glutamate as a source of glutamate. The whole-cell current amplitudes measured by the use of whole-cell current recording in the absence and presence of the nucleic acid are compared. A decrease in whole-cell current in the presence of the nucleic acid indicates that the nucleic acid is a specific glutamate receptor inhibitor.

In another aspect, the invention relates to a method of modulating the function of a glutamate receptor comprising contacting a glutamate receptor with a nucleic acid ligand of the invention that binds to both the open-channel and the closed-channel conformations of the receptor, but only does the binding of the open-channel conformation lead to inhibition of the receptor function.

In yet another aspect, the invention relates to a pharmaceutical composition comprising an isolated nucleic acid of the invention and, optionally, a pharmaceutically acceptable carrier.

In a related aspect, the invention relates to a method of treatment for a disease or condition characterized by excessive activation of ionotropic glutamate receptors, the method comprising administering to the subject in need of such treatment, a therapeutically effective amount of the nucleic acid of the invention. These and other objects, features and advantages of this invention will become apparent from the following detailed description of the various aspects of the invention taken in conjunction with the accompanying drawings.

BRIEF DESCRIPTION OF THE DRAWINGS

FIG. 1 shows enriched RNA sequences obtained from the SELEX process, the number of copies of each and the A/A(I) for each.

FIG. 4 shows the results of a whole-cell current recording assay in which one of the embodiments of the invention, AG56, selectively inhibited the open-channel conformation of all of the AMPA receptor subunits, i.e., GluA1, GluA2, GluA3 and GluA4 (top panel), but it did not inhibit either the kainate receptors (GluK1 and GluK2) or NMDA receptors (GluN1/2A, GluN1/2B) (bottom panel).

FIG. 6 shows the results of homologous competition binding of one of the embodiments of the invention, AG56, in which binding of AG56 to receptor is plotted for both unliganded, closed-channel form (top panel) and open-channel form of GluA2Q$_{flip}$ (bottom panel).

FIG. 10 is a table showing some of the nucleic acid embodiments representative of the invention derived from AG1407.

DETAILED DESCRIPTION OF THE INVENTION

Figure 2:
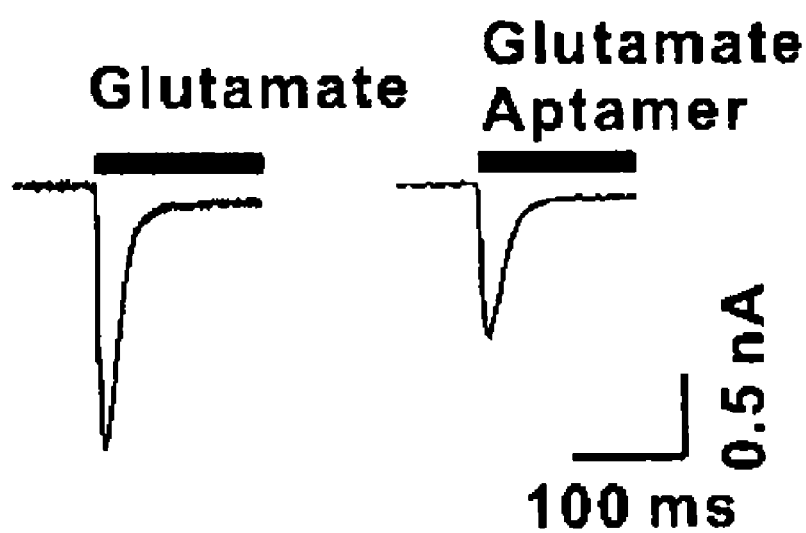
FIG. 2 shows representative traces of the whole-cell current response of GluA2Q$_{flip}$ to 3 mM glutamate in the absence and presence of 500 nM an aptamer of the invention, AG1407. GluA2Q$_{flip}$ represents the unedited, flip spliced isoform of the GluA2 subunit of the AMPA receptors. GluA2Q$_{flip}$ was the target of SELEX.

All patents, publications, applications and other references cited herein are hereby incorporated by reference into the present application. Methodology used in developing the present invention are well known to those of skill in the art and are described, for example, in Sambrook et al., 2001, *Molecular Cloning: A Laboratory Manual*, Third Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984 (M. L. Gait ed.), the contents of which are hereby incorporated by reference. In the description that follows, certain conventions will be followed as regards the usage of terminology.

The term "aptamer" refers to a nucleic acid or oligonucleotide molecule that binds to a specific molecular target such as a receptor protein. Aptamers are obtained from an in vitro evolutionary process known as SELEX (Systematic Evolution of Ligands by Exponential Enrichment), which selects target-specific aptamer sequences from large combinatorial libraries of single stranded oligonucleotide templates comprising randomized sequences. Aptamer compositions may be double-stranded or single-stranded, and may include deoxyribonucleotides, ribonucleotides, nucleotide derivatives, or other nucleotide-like molecules. The nucleotide components of an aptamer may include modified or non-natural nucleotides, for example nucleotides that have modified sugar groups (e.g., the 2'-OH group of a ribonucleotide may be replaced by 2'-F or 2'—NH$_2$), which may improve a desired property, e.g., resistance to ribonucleases or a longer lifetime in biological fluids, such as blood and cerebrospinal fluid. Aptamers may also be conjugated to other molecules, e.g., a high molecular weight carrier to slow clearance of the aptamer from the circulatory system. Aptamers may be specifically cross-linked to their cognate ligands, e.g., by photo-activation of a cross-linker. [Brody, E. N. and L. Gold (2000) J. Biotechnol. 74:5-13.].

The term "nucleic acids," or "oligonucleotides," as used herein, refers to a polymer of nucleotides. Typically, a nucleic acid comprises at least three nucleotides. The polymer may include natural nucleosides (i.e., adenosine, thymidine, guanosine, cytidine, uridine, deoxyadenosine, deoxythymidine, deoxyguanosine, and deoxycytidine) or modified nucleosides. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping. Examples of modified nucleotides include, for example, base modified nucleoside (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyladenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available (e.g. see the following urls: trilinkbiotech-.com, appliedbiosystems.com, biogenex.com or syngendna-.com).

As used herein, a "nucleic acid ligand" is a non-naturally occurring nucleic acid that binds selectively to a target. The nucleic acid that forms the nucleic acid ligand may be composed of naturally occurring nucleosides, modified nucleosides, naturally occurring nucleosides with hydrocarbon linkers (e.g., an alkylene) or a polyether linker (e.g., a polyethylene glycol or PEG linker) inserted between one or more nucleosides, modified nucleosides with hydrocarbon or PEG linkers inserted between one or more nucleosides, or a combination of thereof. In one embodiment, nucleotides or modified nucleotides of the nucleic acid ligand can be replaced with a hydrocarbon linker or a polyether linker provided that the binding affinity and selectivity of the nucleic acid ligand is not substantially reduced by the substitution. The target molecule of a nucleic acid ligand is a three dimensional chemical structure to which the nucleic acid ligand binds. However, the nucleic acid ligand is not simply a linear complementary sequence of a nucleic acid target, but may include regions that bind via complementary Watson-Crick base pairing interrupted by other structures such as hairpin loops. In one embodiment, the nucleic acid ligand binds to a cell surface target for a specific disease state. A preferred target is an "antigen" on the surface of a cell, such as a cell surface receptor, or an ion channel. More preferably, the target is a glutamate receptor relevant to this invention.

In one embodiment, the nucleic acid ligand of the invention is resistant to endonuclease and exonuclease degradation. Typically, nucleic acid ligands that include one or more modified nucleotide exhibit improved resistant to endo- and exonuclease degradation.

Nucleic acid ligands may be prepared by any method. However, in one embodiment, the method of preparing nucleic acid ligands is to identify nucleic acid ligands from a candidate mixture of nucleic acids by Systemic Evolution of Ligands by Exponential Enrichment (SELEX), or a variation thereof, which is a commonly used method of identifying nucleic acid ligands that bind to a target from a candidate mixture of nucleic acids or a nucleic acid library.

The SELEX process for obtaining nucleic acid ligands is described in U.S. Pat. No. 5,567,588, (the contents of which are hereby incorporated by reference) and may include the following steps:

1) A candidate mixture of nucleic acids of differing sequences, for example, a combinatorial RNA library, is prepared, which contains ~$10^{15}$ sequence variations.
2) The candidate mixture is contacted with a target of interest under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.
3) The nucleic acids with the highest affinity for the target are partitioned from those nucleic acids with lesser affinity to the target using known ligands for the receptor. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 0.1%-10%) is retained during partitioning.
4) Those nucleic acids selected during partitioning as having the relatively higher affinity to the target are then amplified to create a new candidate mixture that is enriched in nucleic acids having a relatively higher affinity for the target. The amplification involves reverse-transcription/polymerase chain reaction (RT/PCR), and in vitro transcription to generate a biased library that is richer in the specific sequences than the previous library.
5) By repeating the partitioning and amplifying steps above, the newly formed candidate mixture contains fewer and fewer unique sequences or the unique sequences will become more and more dominant to the composition of the candidate mixture. Consequently, the average degree of affinity of the nucleic acid mixture to the target will generally increase. Taken to its extreme, the SELEX process will yield a candidate mixture containing one or a small number of unique nucleic acids representing those nucleic acids from the original candidate mixture having the highest affinity to the target molecule.

To elucidate the channel opening kinetics of the homomeric channel with and without aptamer ligand, a rapid kinetic technique that has a microsecond time resolution, namely laser pulse photolysis of caged glutamate, is used. The channel opening rate constant ($k_{op}$), the channel closing rate constant ($k_{cl}$) or the lifetime of the channel, and the dissociation equilibrium constant for glutamate ($K_1$) are determined. Thus, by this methodology, the mechanism of action, the affinity, and selectivity of each aptamer on the functional forms of each glutamate receptor subunit can be characterized.

In one aspect, the present invention provides novel nucleic acids that inhibit the activity of ionotropic glutamate receptors, and in particular, the open channel conformation of AMPA receptors. The nucleotide sequences of some examples of nucleic acids of the invention are shown in FIGS. 1 and 10.

The present invention further provides a method of identifying nucleic acids which specifically bind to and inhibit the function of glutamate receptors such as the AMPA receptor. The method comprises first screening a nucleic acid library for a nucleic acid that binds to a glutamate receptor. A modified SELEX method was used to identify the nucleic acid ligands disclosed herein. Once a glutamate receptor-specific aptamer has been identified, the aptamer's ability to inhibit glutamate function is evaluated. By providing a cell that has been transfected to overexpress the glutamate receptor and measuring glutamate-induced whole-cell current in a single cell in the presence and absence of the nucleic acid identified by SELEX, a comparison of the measurement of whole cell current in the presence and absence of nucleic acid is informative of the aptamer's potential as a glutamate receptor inhibitor. A decrease in the whole-cell current in the cell in the presence of nucleic acid as compared to the whole-cell current in the absence of nucleic acid indicates that the nucleic acid inhibits glutamate receptor function.

To arrive at the novel inhibitors of the present invention, therefore, a novel combination of two approaches was used, namely an in vitro iterative procedure, SELEX, to select the aptamers of the invention from a combinatorial RNA library and a laser-pulse photolysis technique that has a µs time resolution to screen the aptamers against a functional (i.e., non-desensitized) form of the glutamate receptor (for more details, see Huang et al. *Potent and Selective inhibition of the Open-Channel Conformation of AMPA Receptors by an RNA Aptamer* Biochemistry in print 2010).

To find inhibitors selectively targeting the open-channel conformation of AMPA receptors, SELEX, an in vitro evolution approach, was used to identify potential RNA inhibitors or aptamers from an RNA library that contained ~$10^{15}$ randomized sequences[9,10]. This approach mimics how immune system works by generating and screening a tremendous number of RNAs to identify a desired RNA molecule(s) with a defined property without pre-existing templates—a concept and practice different from conventional organic synthesis to produce small molecule inhibitors. RNA aptamers can fold into potentially useful three-dimensional structures, and can be evolved using SELEX to recognize virtually any target molecules as well as perform desired functions with high affinity and selectivity not found in nature[11]. Specifically, we chose to use the GluA2Q$_{flip}$ AMPA receptor as the SELEX target, because GluA2 is considered a key subunit that mediates excitotoxicity[12], and the unedited or the Q isoform (i.e., glutamine at the glutamine/arginine or Q/R editing site) is calcium-permeable, whereas the R isoform is not[13]. An abnormal expression of the Q isoform of GluA2 is linked to neurological disorders such as ALS.

The following strategy was employed to make it practically possible to apply SELEX to evolving aptamers against the open-channel conformation of AMPA receptors. First, a saturating agonist concentration was used to "titrate" the receptor population to maximize the fraction of the open-channel conformation[5]. Second, the open-channel conformation lasted only a few milliseconds after glutamate binding, whereas the binding reaction between the receptor and RNA library required at least 30 min to complete. Therefore, it was necessary to "trap" the open-channel conformation long enough for the binding reaction. Based on these requirements, kainate was chosen as the agonist. Kainate is capable of producing a non-desensitizing current response with GluA2 after kainate binds to it, indicative of a persistent existence of the open-channel conformation[16]. Experimentally, the cell membrane containing the GluA2Q$_{flip}$ receptor was preincubated with 1 mM kainate (i.e., this was a saturating concentration). Third, a noncompetitive inhibitor, i.e., GYKI 47409, was used to elute putative RNAs that might bind to the same site or mutually exclusive sites(s). GYKI 47409 is a 2,3-benzodiazepine derivative and has an inhibition constant ($K_I$) of ~3 µM for the open-channel conformation of GluA2Q$_{flip}$ or ~2-fold higher affinity than towards the closed-channel conformation (Weimin Pei and Li Niu, unpublished data). In addition, the GluA2Q$_{flip}$ channels were transiently expressed in human embryonic kidney (HEK-293) cells, and the membrane fragments harboring the entire functional receptors were used for SELEX[15]. To suppress the enrichment of nonspecific RNAs bound to any other "targets", such as lipids, negative selection was done as in rounds 4, 9 and 13, in a total of 14 selection cycles, in which plain HEK-293 cell membrane lacking only the GluA2Q$_{flip}$ receptors was used to absorb these nonspecific RNAs. In contrast, the positive selection rounds involved the use of GYKI 47409 to elute potentially useful RNAs, and these RNAs were amplified by RT-PCR. An enriched RNA library was then transcribed for a new round of selection.

Through multiple rounds of SELEX, seven enriched sequences were identified as shown in FIG. 1. An enriched sequence was one with at least two copies in the entire sequence pool of 83 clones (i.e., 43 clones from round 12 and 40 clones from round 14). The putative inhibitory property of these sequences was then functionally tested by the use of whole-cell current recording with GluA2Q$_{flip}$ expressed in HEK-293 cells[15]. Based on the whole-cell recording results (see representative traces in FIG. 2) or the ratio of the current amplitudes in the absence and presence of an aptamer, A/A(I) (shown on the right in FIG. 1), AG1407, the most enriched sequence, was one of the most potent inhibitors. A further test of AG1407 at the same aptamer concentration but with increasing glutamate concentrations showed that AG1407 inhibited the open-channel, but not the closed-channel, conformation of GluA2Q$_{flip}$ shown in FIG. 8.

Figure 8:
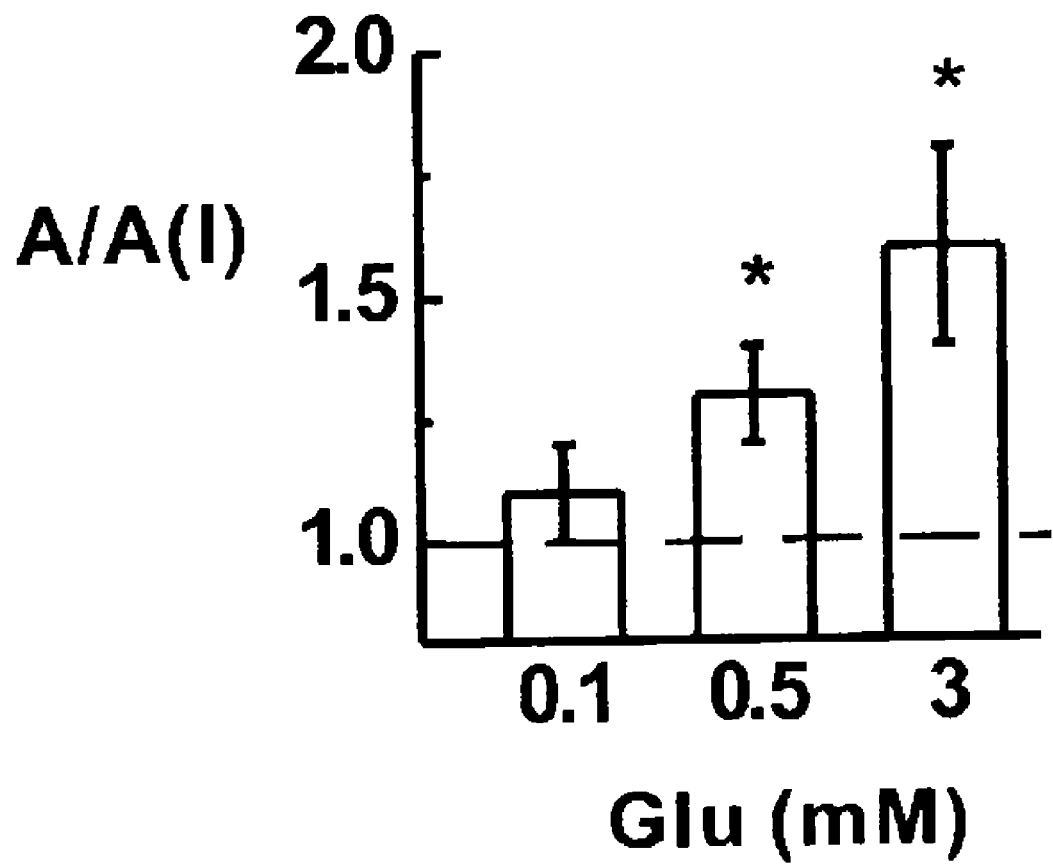
FIG. 8 is a graph showing the inhibition effect of the full length (100 nt) AG1407 on GluA2Q$_{flip}$ receptor channels under different concentrations of glutamate.

The inhibition effect of the full length or 100-nt AG1407 on GluA2Q$_{flip}$ receptor channels under different concentrations of glutamate is shown in FIG. 8. AG1407 inhibited the open-channel state of GluA2 receptor, but not the closed-channel state, as indicated by the whole-cell recording data tested at different concentrations of glutamate. In one-tail student t-test, the A/A(I) value was significantly larger than 1.0 at 0.5 and 3 mM of glutamate (P=0.03 and $1.9 \times 10^{-4}$ respectively), as indicated by an asterisk, but not at 0.1 mM of glutamate (P=0.25) for 0.5 µM of AG1407. Horizontal dashed line represents the A/A(I) value of 1.0, which indicates that there was no inhibition.

Figure 3:
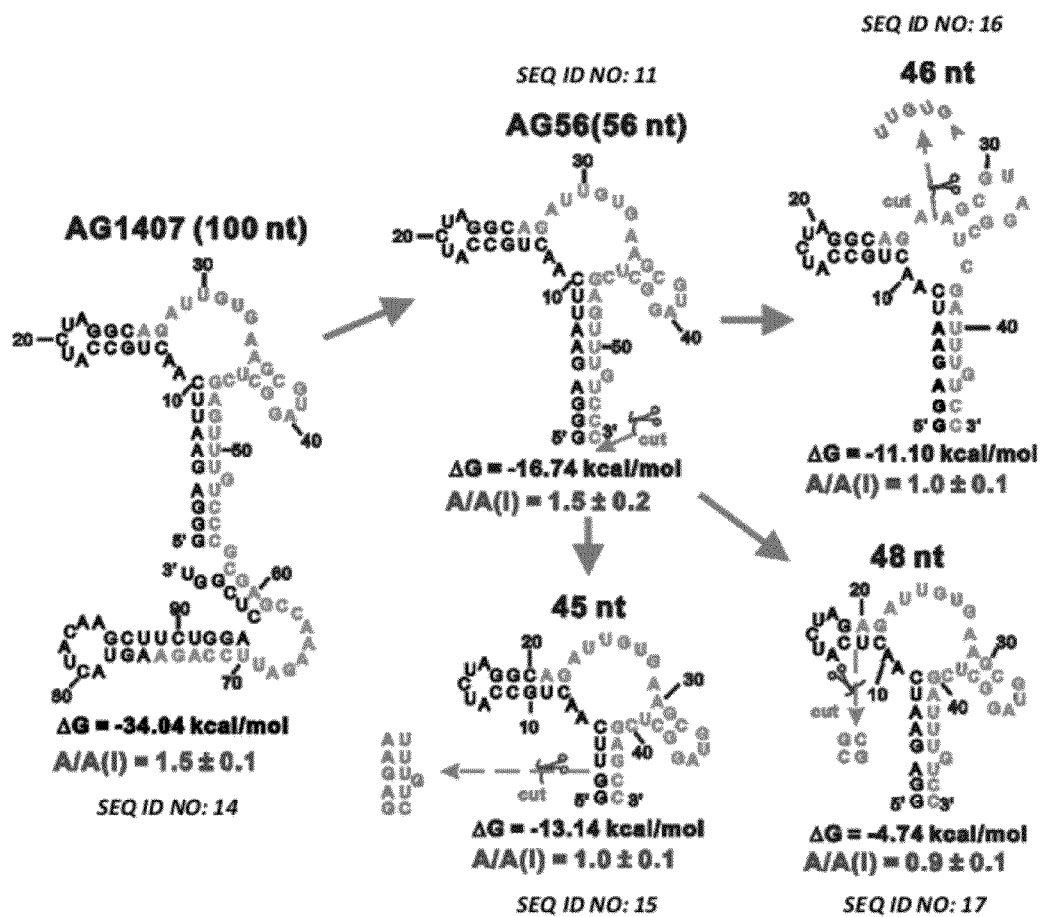
FIG. 3 shows the secondary structures of some of the embodiments of the aptamers of the invention.

Next the 100 nt sequence, AG1407, was systematically truncated to identify the minimal, yet functional sequence. From the secondary structures predicted by Mfold program[17], shorter versions of AG1407 (FIG. 3) were constructed and then functionally tested. Based on A/A(I) value (shown below each predicted structure in FIG. 3), we found the 56-nucleotide (nt) version of AG1407, designated AG56, was a functional sequence. In contrast, shortening the three-way junction by deleting UUGUGA sequence (i.e., the 46 nt RNA) or removing the bulge at the U50 position (i.e., 45 nt RNA) or truncating the base-paired stem in the first stem-loop region (i.e., 48 nt RNA) (FIG. 3) resulted in the total loss of inhibitory function, suggesting that these structural elements are essential in the folding of AG56 as a functional aptamer.

Figure 9:
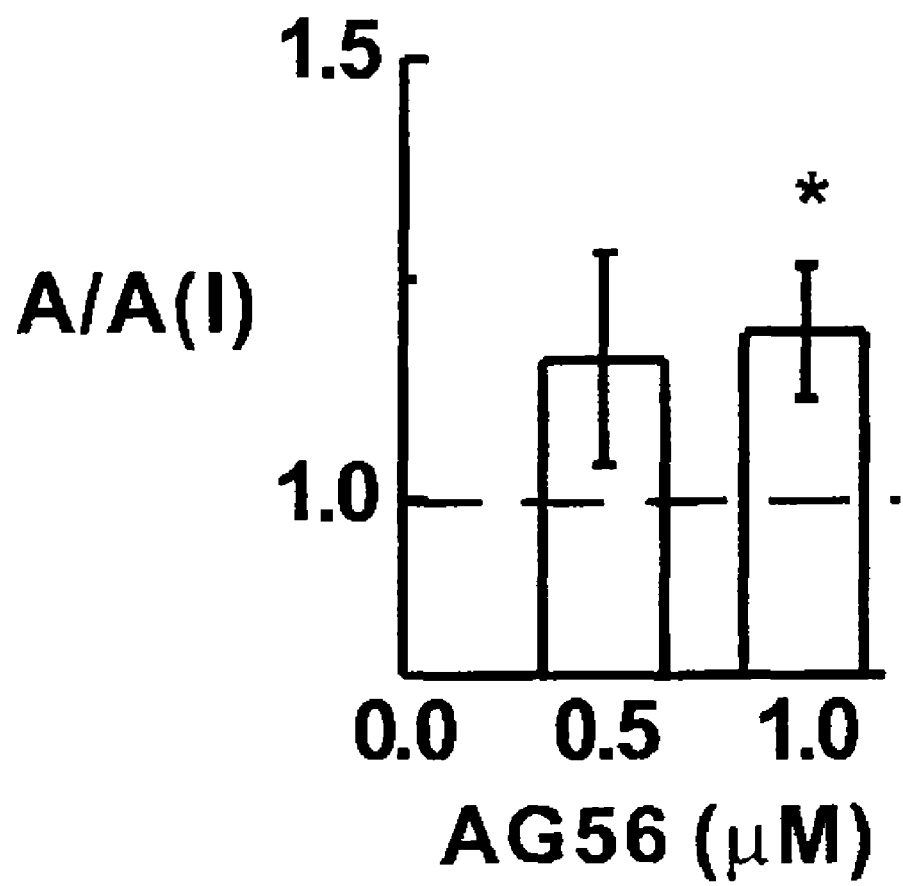
FIG. 9 is a graph showing the inhibition effect of AG56 on the open-channel conformation of the GluA4 receptor subunit.

AG56 was functionally characterized in the following experiments. First, like its predecessor sequence AG1407 (FIG. 8), AG56 selectively inhibited the open-channel, but not the closed-channel, conformation of GluA2Q$_{flip}$ (FIG. 4, top panel). Furthermore AG56 similarly inhibited the open-channel conformation of all other AMPA receptor subunits, i.e., GluA1, 3 and 4, but had no inhibitory effect on any of the closed-channel conformations (FIG. 4 top panel), although the inhibitory effect of AG56 on GluA4 was weak (FIG. 4 top panel). FIG. 9 shows the weak inhibition effect of AG56 on the open-channel conformation of GluA4 receptor subunit. At 0.5 µM of AG56, the A/A(I) was not significantly larger than 1.0 (P=0.08) (see also FIG. 4, top panel and the figure above). AG56 concentration was then increased for the test. At 1 µM of AG56, the A/A(I) ratio was 1.2 (P=0.02), as indicated by the asterisk. Both A/A(I) values at two concentrations of AG56 represents three recordings from three different cells. The glutamate concentration was 3 mM for all points. Horizontal dashed line represents the A/A(I) value of 1.0, i.e., no inhibition.

Glutamate ion channel receptors have three subtypes, NMDA, kainate and AMPA receptors. To make sure that AG56 is AMPA receptor specific, AG56 was also assayed with kainate and NMDA receptor channels. AG56 did not affect either the kainate (i.e., GluK1 and GluK2) or the NMDA receptor channels (i.e., GluN1a/2A and GluN1a/2B) (FIG. 4 bottom panel). It should be noted that GluN1a/2A and GluN1a/2B are two dominant NMDA receptor complexes in vivo[18] and neither GluN1a nor GluN2A or GluN2B can form a functional channel by itself[19]. Taken together, AG56 is an AMPA receptor-subtype selective inhibitor without any unwanted, cross activity on either kainate or NMDA receptor subtypes.

Figure 5:
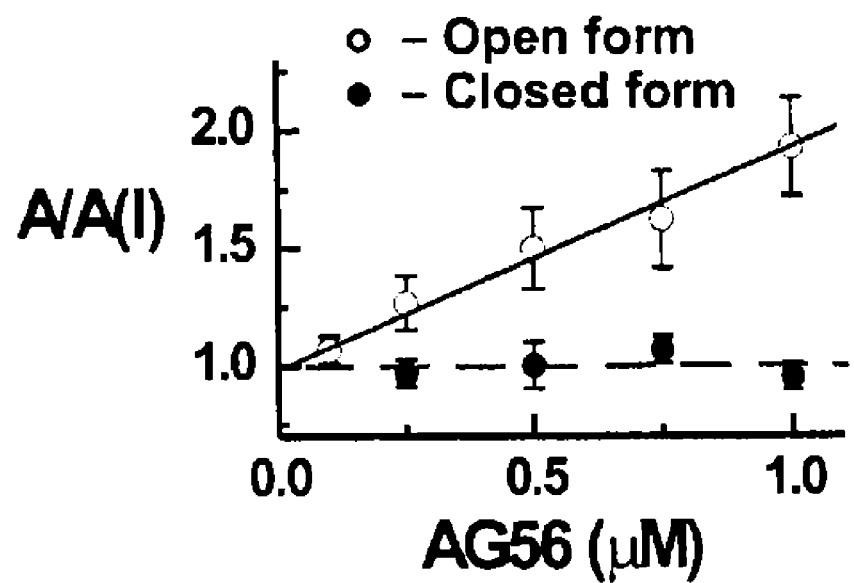
FIG. 5 shows the results of a whole-cell current recording assay in which one of the embodiments of the invention, AG56, inhibited the open-channel conformation as a function of aptamer concentration, but not the closed-channel conformation of GluA2Q$_{flip}$.

Next the mechanism of action of AG56 on the GluA2Q$_{flip}$ receptor channel expressed in HEK-293 cells was elucidated. The inhibition constant of AG56 was first determined to be 0.95±0.20 μM (the solid line in FIG. 5) for the open-channel conformation of GluA2Q$_{flip}$ at 3 mM glutamate concentration where almost all of the channels were in the open-channel conformation (this was because the EC$_{50}$ value of GluA2Q$_{flip}$ with glutamate was 1.3 mM and the channel-opening probability of GluA2Q$_{flip}$ was near unity[20]). In contrast, AG56 did not inhibit the closed-channel conformation or state of GluA2Q$_{flip}$, as verified by a series of aptamer concentrations (FIG. 5). This result could be explained by a noncompetitive mechanism by which AG56 bound to the receptor at its regulatory site, and such a site was accessible from both the closed-channel and the open-channel states or conformations, yet only the open-channel conformation was inhibited[21]. Alternatively, this result could be explained by an uncompetitive mechanism, such as an open-channel blockade model, by which AG56 would only inhibit the open-channel conformation, because the uncompetitive site would only be accessible through the open-channel conformation[22]. To differentiate these two mechanisms, we first carried out a homologous competition binding assay[23] and found that AG56 not only bound to the closed-channel conformation (i.e., the unliganded, closed-channel receptor form) but did so with an affinity, i.e., K$_d$=68±40 nM (FIG. 6 top panel) similar to that for the open-channel conformation, i.e., K$_d$=80±23 nM (FIG. 6 bottom panel). These results were consistent with a noncompetitive mechanism, because AG56 was found to bind to the closed-channel conformation, although it did not inhibit the closed-channel conformation. These results, however, were inconsistent with an uncompetitive mechanism.

Figure 7:
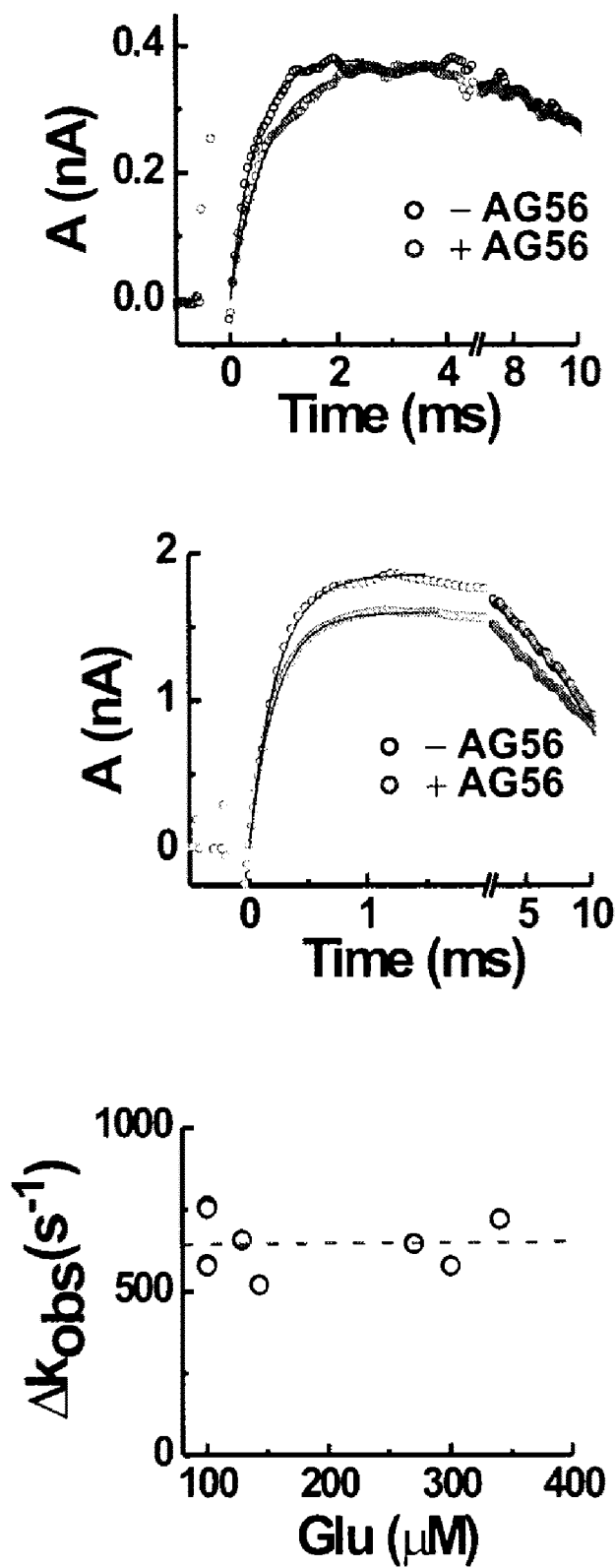
FIG. 7 shows the laser-pulse photolysis measurement of the effect of AG56 on the channel-closing rate constant or $k_{cl}$ and channel-opening rate constant or $k_{op}$ with GluA2Q$_{flip}$.

We further characterized the mechanism of inhibition of AG56 on the channel-opening kinetic process of GluA2Q$_{flip}$. Using a laser-pulse photolysis technique, together with a photolabile precursor of glutamate or caged glutamate, which provided a time resolution of ~30 microsecond[24], we specifically measured the effect of AG56 on both the channel-opening ($k_{op}$) and the channel-closing rate constant ($k_{cl}$)[21] (FIG. 7 left and middle panels). This experiment enabled us to simultaneously follow not only the rate of channel opening but also the current amplitude, prior to channel desensitization[21] (FIG. 7 left and middle panels). As we have shown previously[21], $k_{cl}$ reflects the lifetime (τ) of the open channel (i.e., τ=1/$k_{cl}$) and the effect of an inhibitor on $k_{cl}$ thus reveals whether or not it inhibits the open-channel conformation. In contrast, $k_{op}$ reflects the closed-channel conformation and the effect on $k_{op}$ reveals whether the inhibitor inhibits the closed-channel conformation[21] (see Examples below). Experimentally, at a low glutamate concentration (i.e., 100 μM photolytically released glutamate) where $k_{cl}$ was measured[21], AG56 inhibited the rate of channel closing, consistent with a noncompetitive mechanism by which it inhibited the open-channel form. Yet, AG56 did not affect the current amplitude (FIG. 7 left panel), because the amplitude observed at this low glutamate concentration (i.e., 100 μM photolytically released glutamate) was dominated by the closed-channel receptor population (notice this was consistent with the amplitude measurement shown as the dashed line in FIG. 5). However, when the concentration of glutamate increased and $k_{op}$ became measurable[21], AG56 did not inhibit $k_{op}$ (FIG. 7 middle and right panels). In other words, the inhibition of the rate by AG56 could be completely ascribed to the inhibition on $k_{cl}$ such that the difference between the observed rate constant of channel opening or $\Delta k_{obs}$ in the absence and presence of AG56 at the same AG56 concentration was invariant in spite of increasing glutamate concentration (see FIG. 7 right panel and its legend, and the mechanistic treatment of the rate data, specifically equ. 9, in EXAMPLE below). The lack of an effect of AG56 on $k_{op}$ (FIG. 7 middle and right panels) further demonstrated that AG56 did not inhibit the closed-channel conformation. In contrast, AG56 reduced the current amplitude at a higher glutamate concentration (FIG. 7 middle panel), because the current amplitude at a higher glutamate concentration began to reflect more on the open-channel receptor population. The effect of AG56 on the current amplitude from the rate measurement (FIG. 7 middle panel) was again consistent with the amplitude measurement using a rapid solution flow method (FIG. 5). Taken together, our results, i.e., the binding site assessment (FIG. 6) and the rapid kinetic characterization of the effect of AG56 on both $k_{cl}$ and $k_{op}$ (FIG. 7) as well as the amplitude measurement (FIG. 5) are consistent only with AG56 being a noncompetitive inhibitor selective to the open-channel receptor conformation. This conclusion should not be surprising because 2,3-benzodiazepine compounds like the one we used (i.e., GYKI 47409) in SELEX are known as noncompetitive inhibitors. RNA aptamer AG1407, the predecessor of AG56, which was eluted from GluA2Q$_{flip}$ by GYKI 47409, was supposedly bound to the same noncompetitive site.

Our results here demonstrate that the use of an in vitro evolution method from a random sequence library to identify high affinity, noncompetitive inhibitors of AMPA receptors is not only possible, but also can lead to a discovery of inhibitors with unprecedented properties, such as a unique selectivity towards a specific receptor conformation. Such a property is expected to allow us to control the receptor activity more tightly with minimal or none off-target activity, because of the selective molecular recognition of this aptamer to a specific AMPA receptor conformation or the open-channel conformation. This can be illustrated by the fact that a competitive inhibitor loses its inhibitory potency when agonist concentration increases (because they compete to the same site)[15], whereas AG56, which selectively inhibits the open-channel conformation of AMPA receptor, will continue to be effective when agonist concentration increases (FIG. 5), such as under excitotoxic conditions. In addition, small molecule inhibitors of AMPA receptors, prepared by synthetic chemistry, such as quinoxalines, and 2,3-benzodiazepine compounds, generally have limited water solubility, which so often plagues the clinical usefulness of these compounds[25]. In contrast, RNA aptamers are naturally water soluble. Therefore, the aptamer we discovered represents a water-soluble, highly potent and selective inhibitor that rivals all of the existing, small molecule inhibitors. Next, we will choose a chemically modified random library by replacing, for instance, the 2'-OH group of RNAs with 2'-fluorine group so that the resulting RNAs will become resistant to ribonucleases in vivo. Consequently these chemically modified aptamers will be stable enough in vivo so that their effectiveness in controlling AMPA receptor activities can be tested in vivo.

Aptamers that recognize the AMPA receptors may be selected in a number of ways. In one embodiment, aptamers are selected from a combinatorial library using SELEX, by immobilizing intact cells containing the glutamate receptor on a biosensor chip and monitoring using a surface plasmon resonance (SPR) technique. SPR is an optical technique that offers real time analysis of the rates of adsorption and desorption for a range of surface interactions. In an alternate embodiment, a cell membrane preparation, for example from a cell that has been transfected to overexpress the target receptor, may be used as the selection target.

Known inhibitors for the receptor, for example, NBQX, philanthotoxin-343 and GYKI 47261 are used to displace all specific RNAs previously bound to the receptor. The consensus sequences in the aptamers are then identified by cloning and sequencing to identify inhibitor candidates.

Prior to screening the aptamers for inhibitory activity, the target receptor subunits are expressed at an enhanced efficiency by transfecting cells, for example, HEK-293 cells with a nucleic acid encoding the receptor subunit(s) in conjunction with a nucleic acid encoding simian virus (SV) 40 T antigen. Methods for the construction of an appropriate vector and for transfection of an appropriate host cell are well known to those of skill in the art and are described, for example, in Sambrook et al., 2001, *Molecular Cloning: A Laboratory Manual*, Third Edition, Cold Spring Harbor Laboratory Press, Cold Spring Harbor, N.Y.; *DNA Cloning: A Practical Approach*, Volumes I and II, 1985 (D. N. Glover ed.), the contents of which are hereby incorporated by reference.

Pharmaceutical Compositions

The present invention also includes pharmaceutical compositions comprising the nucleic acid aptamers of the invention. In some embodiments, the compositions are suitable for internal use and include an effective amount of a pharmacologically active compound of the invention, alone or in combination with one or more pharmaceutically acceptable carriers. The compounds are especially useful in that they have very good solubility.

Compositions of the invention can be used in a method for treating a patient or subject having a disease characterized by excessive activation of ionotropic glutamate receptors. Examples of diseases amenable to treatment in accordance with the present invention include amyotrophic lateral sclerosis (ALS), stroke, Alzheimer's disease and Parkinson's syndrome. The method involves administering to the patient or subject a composition comprising a nucleic acid aptamer that binds the receptor involved with the pathology, so that binding of the composition to the target alters the biological function of the target, thereby treating the pathology.

The patient or subject to be treated by the methods of this invention can be a mammal, or more particularly, a human.

In practice, the compounds or their pharmaceutically acceptable salts, are administered in amounts which will be sufficient to exert their desired biological activity, e.g., inhibiting excess activation of AMPA receptors. The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

The magnitude of a prophylactic or therapeutic dose of aptamer in the acute or chronic management of disease will vary with the severity and nature of the condition to be treated and the route of administration. The dose and perhaps the dose frequency will also vary according to the age, body weight and response of the individual patient. It may be necessary to use dosages outside the usual ranges in some cases, as will be apparent to those skilled in the art. Further, it is noted that the clinician or treating physician will know how and when to interrupt, adjust, or terminate therapy in conjunction with individual patient response. The terms "a therapeutically effective amount" and "an amount sufficient to treat conditions characterized by excessive activation of ionotropic glutamate receptors are encompassed by the above-described dosage amounts and dose frequency schedule.

Any suitable route of administration may be employed for providing the patient with an effective dosage of the aptamer of the invention. For example, oral, rectal, parenteral (subcutaneous, intramuscular, intravenous), intrathecal (IT) and/or intracerebroventricular injection (ICV) with the use of infusion pumps, transdermal, aerosol and like forms of administration may be employed. Dosage forms include tablets, troches, dispersions, suspensions, solutions, capsules, transdermal delivery systems, and the like.

The pharmaceutical compositions of the present invention comprise an aptamer of the invention as the active ingredient, and may also contain a pharmaceutically acceptable carrier, and optionally, other therapeutic ingredients.

Example 1

Receptor Preparation

GluA2Q$_{flip}$ receptor was chosen to be the target of the aptamer of the invention. Specifically, GluA2Q$_{flip}$ receptor was transiently expressed in human embryonic kidney (HEK) 293S cells. These cells were co-transfected with the simian virus 40 large T-antigen (TAg) gene to enhance the receptor expression, in accordance with materials and methods known to those of skill in the art. For SELEX, the membrane-bound GluA2Q$_{flip}$ receptors were harvested 48 hours after transfection[2]. Specifically, the HEK-293 S cells were homogenized briefly in a cold, 50 mM Tris-acetate buffer (pH 7.4) containing 10 mM EDTA and 1 mM phenylmethanesulphonyl fluoride (PMSF). Large membrane pieces were removed by a low-speed spin at 1000 g for 10 min. The supernatant was centrifuged again at >20,000 g for 30 min. The pellet was washed twice with cold 50 mM Tris-acetate buffer (pH7.4). Before using for SELEX, the cell membrane pellet was resuspended in 1×extracellular buffer, which contained (in mM) 150 NaCl, 3 KCl, 1 CaCl$_2$, 1 MgCl$_2$, 10 HEPES (pH 7.4).

Example 2

Aptamer Selection by SELEX

The operation of SELEX is well known in the art and has been described previously[3]. In the initial round of SELEX, a combinatorial RNA library (previously described) with ~10$^{15}$ random sequences was first dissolved in 1×extracellular buffer (see EXAMPLE 1). The RNA library was incubated at 70° C. for 10 min and then left at room temperature for 20 min before being mixed with the receptors. The final concentration of membrane-bound receptor in the binding mix was 8 nM, as determined by [$^3$H]AMPA binding. To keep the homomeric GluA2Q ion channels at the open-channel conformation or state, the membrane-bound receptor was exposed to 1 mM (final concentration) of kainate for 5 min before mixing with the RNA library.

The mixture of the RNA library and the receptor was incubated at 22° C. for 50 min for RNA binding to the receptor in the presence of 0.3 units/μl RNase inhibitor. After binding, the mixture was passed through a 25 mm diameter nitrocellulose filter. The filter was immediately washed with 15 ml of 1×extracellular buffer. In the first 4 rounds, the bound RNA molecules were collected from the nitrocellulose filter by immersing the filter in 500 μl of denaturing buffer containing 8 M urea in 10 mM Tris, and then by extracting the RNA using the standard phenol/chloroform extraction/precipitation protocol. Starting from the 5$^{th}$ round, we eluted the desired RNAs bound to the receptors, which were blocked on the filter, by using 1-mM (final concentration) GYKI 47409 in 1×extracellular buffer. The RNA in the collected elution solution was then recovered by precipitation. These RNAs were then subject to reverse transcription and PCR. A new RNA library was made by in vitro transcription reaction for the next round of SELEX. Among the 14 selection rounds we carried out for the selection of AG1407, rounds 4, 9, and 13 were negative selection cycles in which plain HEK-293S cell membrane fragments were used in the binding reaction to "absorb" nonspecific RNAs targeting anything but the GluA2Q$_{flip}$ receptors. At the end of the 14th SELEX round, the DNA pools from rounds 12 and 14 were separately cloned into the pGEM-T easy vector (Invitrogen) for sequencing. After sequencing and sequence comparison, the enriched sequences from all of the cloned sequences were identified (see FIG. 1). Specifically, the variable region (N50) of an RNA sequence is shown (with corresponding designation, e.g., AG1407) whereas the 5' and 3' constant regions are displayed below. The copy number, shown on the right, represents the number of appearances of the same sequence in the entire sequence pool. The putative inhibitory functions of these RNAs were assayed (as described below by using whole-cell current recording). Inhibition by these sequences of GluA2Q$_{flip}$, the SELEX target, as tested by whole-cell recording, is shown, on the right, as the ratio of the whole-cell current amplitude in the absence and presence of 500 nM of aptamer, A/A(I), at 3 mM glutamate.

Representative traces of the whole-cell current response of GluA2Q$_{flip}$ to 3 mM glutamate in the absence and presence of AG1407 is shown in FIG. 2. The current was recorded at −60 mV, pH 7.4 and room temperature with the same HEK-293 cell expressing GluA2Q$_{flip}$.

Example 3

RNA Purification

All RNA aptamer samples were in vitro transcribed and purified for quantitative assay. An RNA sample dissolved in 1 ml of 10 mM Tris-HCl buffer (pH 7.4) was loaded onto a Q anion exchange column (Bio-Rad). The column was then washed with 25 mM Tris-HCl buffer (pH7.4) for 30 min at a flow rate of 1 ml/min. The aptamer was eluted by running 1.5 M NaCl in 25 mM Tris-HCl buffer at the same flow rate. The aptamer sample was then dialyzed in the extracellular buffer for whole-cell current recording assays, described below.

Example 4

Homologous Competitive Binding Assay

Whether AG56 bound to the close-channel state or conformation, and if so, the affinity of binding were assayed by homologous competitive binding assay using $^{32}$P-label$^4$. To do this, RNA was first dephosphorylated by using calf intestinal phosphatase (CIP), prior to the 5'-end $^{32}$P-labeling$^5$. Labeled RNA was passed through a NucAway spin column (Applied Biosystem) to remove excess γ-$^{32}$P-ATP. Then, 1 μl of 10 nM of $^{32}$P-labeled aptamer was mixed with 2 μg of yeast tRNA (Sigma) and a series of concentrations of unlabeled (cold) aptamer whose concentrations varied from 0-400 nM in the final reaction mix. The mixed aptamer sample was incubated first at 70° C. for 10 min and then at room temperature for 20 min, before mixed with the receptor. For receptor preparation, 4 femtomol of the membrane-bound receptor was resuspended in 1× extracellular buffer with and without 1 mM of kainate (which corresponded to the open-channel state and the closed-channel state, respectively; for the latter, it corresponded to precisely the unliganded, closed-channel state). The final concentration for the receptor and for the hot aptamer, after mixing, was 0.4 nM and 0.1 nM, respectively. The mixture was incubated at 22° C. for 1 hour for binding. Then the mixture was loaded onto a pre-soaked 0.45 μm nylon filter (VWR), which was then centrifuged at 4000 rpm for 5 min. The filter was washed twice with 400 μl of 1×extracellular buffer. The radioactivity on the filter was quantified in a scintillation counter (Beckman LS6500). The non-specific binding was estimated using equation 1 below. The specific binding was obtained by using the total binding count or counts per min (CPM) minus the estimated non-specific CPM. Furthermore, the specific binding was normalized to percentage based on the data without the competitor or the cold or non-labeled AG56. Assuming a one-site binding model, the $K_d$ of AG56 binding to a particular GluA2Q$_{flip}$ receptor conformation was estimated by fitting of the binding data to equ. 1

$$Y = \frac{B_{max} \times [\text{Hot}]}{[\text{Hot}] + [\text{Cold}] + K_d} + NSB \qquad \text{equ. 1}$$

where [Hot]/[Cold] are the concentrations of the unbound, hot AG56/unlabeled or AG56, respectively; NSB represents non-specific binding.

Example 5

Cell Culture and Transient Expression of Receptors for Whole-Cell Recording

The original cDNAs in pBlueScript encoding rat GluA1, 2 and 3 AMPA receptors and GluK2 kainate receptor were kindly provided by Steve Heinemann. The GluA4 DNA plasmid was kindly provided by Peter Seeburg. The GluK1 plasmid was kindly provided by Geoffrey Swanson. The cDNAs of all three NMDA receptor subunits were gifts from John Woodward. All DNA plasmids were propagated using Escherichia coli host (DH5α) and purified using QIAGEN DNA purification kits.

All of the receptors were transiently expressed in HEK-293S cell. HEK-293S cells were maintained in Dulbecco's modified Eagle's medium (DMEM) supplemented with 10% fetal bovine serum and 1% penicillin in a 37° C., 5% $CO_2$, humidified incubator. Receptors were transiently transfected by using calcium phosphate or lipofectamine 2000 (Invitrogen). The DNA plasmids encoding green fluorescent protein (GFP) and T-antigen (TAg) were cotransfected in HEK-293 S cells. GFP was used as a transfection marker for cell recording, and TAg was cotransfected to potentiate the receptor expression at the single-cell level[6]. Transfected cells were allowed to grow for 48 hour before they were used for recording.

Example 6

Whole-Cell Current Recording

The procedure for whole-cell current recording to assay the inhibitory property of an RNA aptamer is known to those of skill in the art and has been previously described[7]. The electrode for whole-cell recording had a resistance of ~3 MΩ, when filled with the electrode solution (in mM): 110 CsF, 30 CsCl, 4 NaCl, 0.5 $CaCl_2$, 5 EGTA, and 10 HEPES (pH 7.4 adjusted by CsOH). The extracellular buffer composition is described above (see "Receptor Preparation"). For recording of the NMDA channels, the intracellular solution contained (in mM) 140 CsCl, 1 $MgCl_2$, 0.1 EGTA, and 10 HEPES (pH 7.2 adjusted by $Mg(OH)_2$), while the extracellular solution contained (in mM) 135 NaCl, 5.4 KCl, 1.8 $CaCl_2$, 10 glucose and 5 HEPES (pH 7.2 adjusted by NaOH). In the extracellular buffer, 2 μM of glycine was added (glycine was the co-agonist of NMDA receptor)[2]. All reagents including aptamer were dissolved in the corresponding extracellular buffer and used. A U-tube flow device[8] was used to apply glutamate in the absence and presence of aptamer to a cell expressing the receptor of interest. The whole-cell current was recorded using an Axopatch-200B amplifier at a cutoff frequency of 2-20 kHz by a built-in, eight-pole Bessel filter and digitized at 5-50 kHz sampling frequency using a Digidata 1322A from Axon Instruments (Molecular Devices, Sunnyvale, Calif.). The pClamp 8 software (Molecular Devices) was used for data acquisition. All whole-cell recordings were at −60 mV and 22° C.

Example 7

Statistical Data Analysis

Unless noted otherwise, each data point, such as A/A(I) value shown in all of the biological functional assay plots or binding data point, was an average of at least three measurements collected from at least three cells. Origin 7 was used for data analysis and plotting. Uncertainties reported refer to standard deviation from the mean. Student's t tests were performed for some of our data. The significance of inhibition was evaluated by a one-sample two-tailed Student's t test with the assumption that $H_0$: $\mu = \mu_0 = 1$, 1 being the theoretical value of no inhibition and indicated by single ($P \leq 0.05$) or double ($P \leq 0.01$) asterisk sign. The significance of the difference between the open-channel and the closed-channel conformations was evaluated by a two-sample two-tailed Student's t test with the assumption that $H_0$: $\mu_1 = \mu_2$ and indicated by single ($P \leq 0.05$) or double ($P \leq 0.01$) asterisk sign.

Example 8

Laser-Pulse Photolysis Measurements

The use of the laser-pulse photolysis technique to measure the channel-opening kinetics has been described[7]. Briefly, caged glutamate[9] (Invitrogen, Carlsbad, Calif.) was dissolved in the extracellular buffer and applied to a cell using a flow device[8] (see below). In the laser-pulse photolysis measurement of channel opening, a single laser pulse at 355 nm with a pulse length of 8 ns was generated from a pulsed Q-switched Nd:YAG laser (Continuum, Santa Clara, Calif.). The pulse energy varied in the range of 200-800 μJ, measured at the end of an optical fiber (300 μm core diameter) into which the laser was coupled. To calibrate the concentration of photolytically released glutamate, we applied two solutions of free glutamate with known concentrations to the same cell before and after a laser flash[10]. The current amplitudes obtained from this calibration were compared with the amplitude from the laser measurement with reference to the dose-response relationship. These measurements also allowed us to monitor any damage to the receptors and/or the cell for successive laser experiments with the same cell[7].

To deliver AG56 to a HEK-293 cell, a "Ψ"-shaped flow device was used. The central tubing in the Ψ device was filled with the inhibitor solution for preincubation such that the solution was applied prior to the application of free glutamate as the control or free glutamate but mixed with the same inhibitor at the same concentration. In all experiments reported in this study, a 6-second preincubation flow protocol was used for full aptamer preincubation. When free glutamate was used to induce the receptor response in the absence and presence of an aptamer, the amplitude of the whole-cell current observed using the flow device was corrected for receptor desensitization by a method previously described[8]. The corrected current amplitude was used for data analysis.

Example 8

Experimental Design and Data Analysis

The key to characterizing the mechanism of inhibition for AG56 was the laser-pulse photolysis experiment with the use of caged glutamate, which provided a time resolution of ~30 μs[7], described above. The use of this technique allows the investigation of the effect of AG56 on the channel-opening kinetic mechanism of the $GluA2Q_{flip}$ receptors. Before describing how the mechanism of inhibition is elucidated, the kinetic characterization of channel-opening rate process is presented.

1. Mechanism of Channel Opening

Using the laser-pulse photolysis technique, we have previously determined the rate constants for the opening of the $GluA2Q_{flip}$ receptor channels[7], based on a general mechanism of channel opening, shown below.

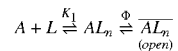

$$A + L \underset{}{\overset{K_1}{\rightleftharpoons}} AL_n \underset{}{\overset{\Phi}{\rightleftharpoons}} \overline{AL_n}_{(open)}$$

A represents the active form of the receptor, L, the ligand, $AL_n$ the closed-channel forms, and $\overline{AL_n}$ the open-channel form, $K_1$ the intrinsic dissociation constant of activating ligand and Φ the channel opening equilibrium constant ($\Phi^{-1}=k_{cl}/k_{op}$). Based on this mechanism and the assumption that the ligand-binding rate was fast as compared to the channel opening, the observed rate constant of channel opening or $k_{obs}$ can be formulated as in equ. 2.

$$k_{obs} = k_{cl} + k_{op}\left(\frac{L}{K_1 + L}\right)^n \quad \text{equ. 2}$$

$$I_t = I_{max}[1 - \exp(-k_{obs}t)] \quad \text{equ. 3}$$

In equ. 2, $k_{cl}$ is the channel-closing rate constant or the lifetime of the channel, τ (τ=1$k_{cl}$), $k_{op}$ is the channel-opening rate constant, and n the number of the ligand molecules to bind to the receptor complex to open the channel (i.e., n=1-4). $I_{max}$ is the maximum current amplitude, and L is the current amplitude at time t. Our previous studies of AMPA receptors, including a mutant AMPA receptor, for their channel-opening kinetic mechanisms led us to conclude that binding of two glutamate molecules per receptor complex (i.e., n=2) was sufficient to induce the channel opening[12].

FIG. 7 shows the laser-pulse photolysis measurement of the effect of AG56 on the channel-closing rate constant or $k_{cl}$ (left panel) and channel-opening rate constant or $k_{op}$ (middle panel) with GluA2Q$_{flip}$ expressed in HEK-293 cells. Specifically, at 100 μM photolytically released glutamate concentration, the $k_{obs}$ value, which reflected $k_{cl}$, was decreased from 2,200 s$^{-1}$ (control or −0.75 μM AG56, black/upper trace, left panel) to 1,600 s$^{-1}$ (+0.75 μM AG56, gray/lower trace, left panel). At 340 μM photolytically released glutamate concentration, the $k_{obs}$ value, which reflected $k_{op}$ (middle panel), was 5,128 s$^{-1}$ and 4,405 s$^{-1}$ in the absence and presence of 0.75 μM AG56. The difference, however, or $\Delta k_{obs}'=k_{obs}-k_{obs}'=\Delta k_{cl}$ was invariant even when glutamate concentration increased (the right panel). Here $\Delta k_{cl}=k_{cl}-k_{cl}'$ where $k_{cl}'$ is the inhibited $k_{cl}$ value and the $k_{cl}$ is the channel-closing rate constant without AG56 (see equ. 9 and the detailed explanation below).

By this plot, AG56 did not inhibit $k_{op}$ (each data point represents at least one measurement from a single cell where $k_{obs}$ is the control rate constant and $k_{obs}'$ is the rate constant in the presence of 0.75 μM AG56). As shown in the left and middle panels of FIG. 7, the whole-cell current rise from the GluA2Q$_{flip}$ channel induced by photolytically released glutamate reflected the channel opening, whereas the current fall was due to channel desensitization. A single-exponential rate law, as shown in equ. 3, was adequate to describe >95% of the rising phase at all the concentrations of photolytically released glutamate, ranging from 100 to 380 μM. This observation was consistent with the assumption that the rate of ligand binding was fast relative to channel opening. Using this technique, we have previously measured the channel-opening kinetics of the GluA2Q$_{flip}$ receptor and have already reported that the $k_{op}$ of (8.0±0.49)×10$^4$ s$^{-1}$ and the $k_{cl}$ of (2.6±0.20)×10$^3$ s$^{-1}$, respectively[7].

It should be pointed out that in equ. 2, when L<<$K_1$, equ. 1 can be reduced to $k_{obs} \approx k_{cl}$. For GluA2Q$_{flip}$, we found previously that $k_{cl}$ was numerically equal to the $k_{obs}$ value obtained at the 100-μM glutamate concentration, which corresponded to ~4% of the fraction of the open-channel form[7].

2. Investigation of the Mechanism of Inhibition by Rate Measurement

The mechanism of inhibition was characterized by studying the effect of an inhibitor such as AG56 on the channel-opening rate process[13,14]. In general there are three ways in which an ion channel receptor can be inhibited. For instance, an inhibitor binds only to the open-channel state or conformation and then inhibits it (Mechanism 1, uncompetitive mechanism of inhibition or open-channel blockade). Alternatively, an inhibitor binds to both the closed- and open-channel states through a regulatory site (Mechanism 2, noncompetitive mechanism). The observed rate constant, $k_{obs}$ in the presence and absence of an inhibitor can be measured using equ. 3. The relationship between $k_{obs}$ and the molar concentration of the ligand (glutamate), L, and the inhibitor, I, can be written according to the individual mechanism, i.e., equ. 4 for mechanism 1, and equ. 5 for mechanism 2.

Mechanism 1

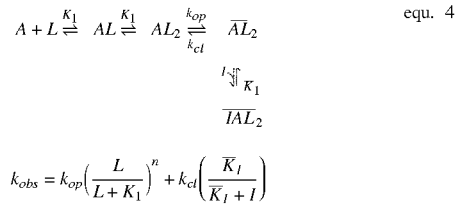

$$k_{obs} = k_{op}\left(\frac{L}{L+K_1}\right)^n + k_{cl}\left(\frac{\overline{K_I}}{\overline{K_I}+I}\right)$$

Mechanism 2

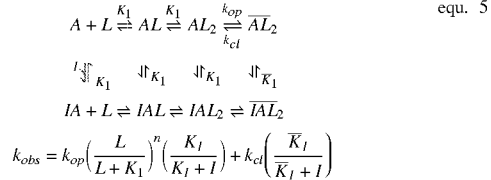

$$k_{obs} = k_{op}\left(\frac{L}{L+K_1}\right)^n \left(\frac{K_I}{K_I+I}\right) + k_{cl}\left(\frac{\overline{K_I}}{\overline{K_I}+I}\right)$$

In deriving these equations, one binding site for inhibitor per receptor molecule is assumed. At low concentrations of glutamate (L<<$K_1$), $k_{obs}$ reflects the channel-closing rate constant since the contribution of the $k_{op}$ portion in equs. 4 or 5 to the overall rate, $k_{obs}$, is negligible. Under this condition, the effect of the inhibitor on the $k_{cl}$ can be measured[13]. Specifically, for both Mechanisms 1 and 2, the effects of the inhibitor on $k_{cl}$ are the same, and can be obtained by equ. 6, which can be derived from either equ. 4 or 5. From equ. 6, the equilibrium dissociation constant of the inhibitor from the open-channel state, $\overline{K_I}$, can be determined. We have previously shown that the $k_{obs}$ value obtained at 100 μM glutamate concentration for GluA2Q$_{flip}$ reflects the $k_{cl}$[7].

$$k_{obs} = k_{cl}\left(\frac{\overline{K_I}}{\overline{K_I}+I}\right) \quad \text{equ. 6}$$

Here in our experiment, the fact that we observed the inhibition of AG56 on $k_{cl}$ suggested that AG56 inhibited the open-channel conformation of the GluA2Q$_{flip}$ receptor (see FIG. 7, left panel). Not surprisingly, AG56 also bound to the open-channel conformation (see FIG. 6, bottom panel).

The effect of an inhibitor on $k_{op}$ is obtained at a high glutamate concentration (where $k_{obs}>k_{cl}$). For Mechanism 1 or uncompetitive mechanism, the inhibitor does not affect $k_{op}$(equ. 7). The lack of inhibition of the closed-channel conformation, manifested by the lack of inhibition on $k_{op}$, is apparently due to the fact that the inhibitor does not even bind to the closed-channel conformation (see Mechanism 1 above). In this case, however, AG56 did bind to the closed-channel conformation (FIG. 6, top panel), and this result was inconsistent with the uncompetitive mechanism of inhibition, described above.

$$k_{obs} - k_{cl}\left(\frac{\overline{K_I}}{\overline{K_I}+I}\right) = k_{op}\left(\frac{L}{L+K_1}\right)^n \quad \text{equ. 7}$$

For Mechanism 2 or a noncompetitive mechanism of inhibition, the inhibitor will affect $k_{op}$ additionally (equ. 8), if $K_I < I$, I being the molar concentration used to measure the $K_I$ value. Consequently the dissociation constant of the inhibitor for the closed-channel conformation can be further determined for Mechanism 2. It should be emphasized that the presence of an inhibitory effect of a noncompetitive inhibitor is due to the fact that the inhibitor must first bind to the closed-channel conformation, as illustrated in Mechanism 2, shown above.

$$k_{obs} - k_{cl}\left(\frac{\overline{K_I}}{\overline{K_I}+I}\right) = k_{op}\left(\frac{L}{L+K_1}\right)^n\left(\frac{K_I}{K_I+I}\right) \quad \text{equ. 8}$$

If, however, the inhibitory effect on the closed-channel conformation is so weak, the inhibitor literally no longer inhibits the closed-channel conformation (but still binds to the site). Under this circumstance, the difference in $k_{obs}$ at a defined ligand concentration in the absence (as illustrated in equ. 2, which we termed as $k_{obs}$) and presence of a noncompetitive inhibitor (as illustrated in equ. 5, which we termed as $k_{obs}'$) would be independent of the ligand concentration. This can be illustrated by (equ. 2-equ. 5), which gives rise to equ. 9:

$$\Delta k_{obs} = k_{obs} - k_{obs}' = \left[k_{op}\left(\frac{L}{L+K_1}\right)^n + k_{cl}\right] - \left[k_{op}\left(\frac{L}{L+K_1}\right)^n\left(\frac{K_I}{K_I+I}\right) + k_{cl}\left(\frac{\overline{K_I}}{\overline{K_I}+I}\right)\right] \quad \text{equ. 9}$$

Thus, $$\Delta k_{obs} = k_{cl} - k_{cl}\left(\frac{\overline{K_I}}{\overline{K_I}+I}\right) = \Delta k_{cl}$$

In arriving at equ. 9, we assumed that $K_I \gg I$; thus the $k_{op}$ portions are canceled off. Based on equ. 9, a plot of $\Delta k_{obs} = k_{obs} - k_{obs}' = \Delta k_{cl}$ vs. glutamate concentration would be invariant under the same inhibitor concentration despite the fact that glutamate concentration was varied. This was exactly the case with AG56 (see FIG. 7, right panel). Our results suggest that AG56 is bound to the closed-channel conformation (FIG. 6, top panel) as a noncompetitive inhibitor, but the binding to the closed-channel conformation of GluA2Q$_{flip}$ is not efficacious or not inhibitory to the function of the receptor channel. Therefore, our results, i.e., our binding data and the rapid kinetic measurements on the effect of AG56 on $k_{cl}$ and $k_{op}$, are consistent with AG56 as a noncompetitive inhibitor. Conversely, these results are inconsistent with an uncompetitive mechanism of inhibition.

3. The Mechanism Investigation by Amplitude Measurement

The method of model differentiation described above concerns only the measurement of rate constants. However, the ratio of the current amplitude in the absence and presence of an inhibitor or apatmer is not only informative but also diagnostic. The amplitude ratio can be used to independently obtain affinity constants for inhibitors and to verify them with those obtained from rate constant measurements. Experimentally, both the rate constant and the maximum current amplitude were collected, and both were used (see FIG. 5 and FIG. 7).

The experimental design of using current amplitude (A) to determine the inhibition constant for both the open-channel and the closed-channel conformations or states required varying concentration of glutamate (see equ. 10a and 10b).

$$\frac{A}{A(I)} = 1 + I\frac{(\overline{AL_2})}{K_{I,app}} \quad \text{equ. 10a}$$

$$(\overline{AL_2}) = \frac{\overline{AL_2}}{A + AL + AL_2 + \overline{AL_2}} = \frac{L^2}{L^2(1+\Phi) + 2K_1L\Phi + K_1^2\Phi} \quad \text{equ. 10b}$$

Determination of $K_{I,app}$ by the ratio of the current amplitude in the absence and presence of inhibitor or A/A(I)—see FIG. 5 in the text. Equ. 10a and 10b were derived based on one inhibitor binding to the receptor. $K_{I,\ app}$ is the apparent inhibition constant for the inhibitor; other terms have been defined previously.

Specifically, at low glutamate concentrations (i.e., $L \ll K_1$), the majority of the receptors were in the closed-channel conformation. Under this condition, the inhibition constant for the closed-channel conformation was determined from the ratio of the amplitude according to equ. 10a and 10b. Likewise, at a saturating ligand concentration (i.e., $L \gg K_1$), the majority of the receptors were in the open-channel state. Consequently, the inhibition constant associated with the open-channel conformation was measured. The basis of using the two ligand concentrations that corresponded to ~4% and ~96% fraction of the open-channel receptor form[7] to determine the corresponding inhibition constant was a putative difference in inhibition constant between the closed-channel and the open-channel conformation. At those low and high ligand concentrations[7], the apparent inhibition constants obtained were considered pertinent to the closed-channel and the open-channel conformations, respectively. Examples of using the current amplitude to determine the inhibition constant for an inhibitor include our previous study of two 2,3-benzodiazepine derivatives with the GluA2Q$_{flip}$ AMPA receptor[15].

We claim:

1. A synthetic nucleic acid that binds to an open-channel conformation of a glutamate ion channel receptor, said nucleic acid comprising the nucleotide sequence of SEQ ID NO: 1.

2. The synthetic nucleic acid of claim 1, comprising a nucleotide sequence selected from the group consisting of SEQ ID NO: 9, SEQ ID NO: 10, SEQ ID NO: 11, SEQ ID NO: 12, SEQ ID NO: 13 and SEQ ID NO: 14.

3. The synthetic nucleic acid of claim 1, wherein the nucleic acid is RNA.

4. The synthetic nucleic acid of claim 1, wherein the nucleic acid contains between 50 and 110 nucleotides.

5. The synthetic nucleic acid of claim 1, wherein the nucleic acid contains between 56 and 100 nucleotides.

6. The synthetic nucleic acid of claim 1, wherein said nucleic acid contains one or more chemically modified nucleotides.

7. The synthetic nucleic acid of claim 1 wherein the one or more chemically modified nucleotides has a 2' fluoro substituent.

8. The synthetic nucleic acid of claim 1, wherein said nucleic acid inhibits glutamate receptor function.

9. The synthetic nucleic acid of claim 1, wherein said nucleic acid has a $K_I < 1$ μM.

10. A composition comprising a synthetic nucleic acid of claim 1 and further comprising one or more synthetic nucleic acids comprising one or more nucleotide sequences selected from the group consisting of SEQ ID NO: 2, SEQ ID NO: 3, SEQ ID NO: 4, SEQ ID NO: 5, SEQ ID NO: 6, and SEQ ID NO: 7.

11. The composition of claim 10, wherein said synthetic nucleic acids have different nucleotide sequences.

12. The isolated nucleic acid of claim 1 wherein the glutamate receptor is of the α-amino-3-hydroxy-5-methyl-4-isoxazole propionic acid (AMPA) subtype.

13. A method of inhibiting the function of a glutamate receptor comprising contacting said receptor with a synthetic nucleic acid of claim 1.

14. The method of claim 13, wherein the glutamate receptor is of the AMPA subtype.

15. A method of inhibiting a glutamate receptor comprising contacting said receptor with the nucleic acid of claim 1.

16. The method of claim 15, wherein the glutamate receptor is of the AMPA subtype.

17. A pharmaceutical composition comprising a nucleic acid according to claim 1 and a pharmaceutically acceptable carrier.

18. An isolated DNA that codes for an RNA wherein the RNA comprises a nucleotide sequence selected from the group of SEQ ID NOS: 1 and 9 to 14.

* * * * *

SEQUENCE LISTING

<160> NUMBER OF SEQ ID NOS: 17

<210> SEQ ID NO 1
<211> LENGTH: 50
<212> TYPE: RNA
<213> ORGANISM: Artificial

```
<220> FEATURE:
<221> NAME/KEY: misc_feature
<222> LOCATION: (1)..(50)
<223> OTHER INFORMATION: aptamer that binds to glutamate receptor, AMPA
      subtype

<400> SEQUENCE: 1
agauugugaa gcguaggcuc gaguuugucc cgcgagccaa agauuccaga                    50

<210> SEQ ID NO 2
<211> LENGTH: 50
<212> TYPE: RNA
<213> ORGANISM: Artificial
<220> FEATURE:
<221> NAME/KEY: misc_feature
<222> LOCATION: (1)..(50)
<223> OTHER INFORMATION: aptamer that binds to glutamate receptor, AMPA
      subtype

<400> SEQUENCE: 2
uugaguugga ugccugcgcu uaacugcgcg acuuauccag agguauacgu                    50

<210> SEQ ID NO 3
<211> LENGTH: 50
<212> TYPE: RNA
<213> ORGANISM: Artificial
<220> FEATURE:
<221> NAME/KEY: misc_feature
<222> LOCATION: (1)..(50)
<223> OTHER INFORMATION: aptamer that binds to glutamate receptor, AMPA
      subtype

<400> SEQUENCE: 3
uacgcugacc uuaccccaca aaaggggacc acgccaacgu aagcgacaga                    50

<210> SEQ ID NO 4
<211> LENGTH: 50
<212> TYPE: RNA
<213> ORGANISM: Artificial
<220> FEATURE:
<221> NAME/KEY: misc_feature
<222> LOCATION: (1)..(50)
<223> OTHER INFORMATION: aptamer that binds to glutamate receptor, AMPA
      subtype

<400> SEQUENCE: 4
cccagacacg gcaguaaaga gaagacuucc agaaaaaagg ggcaaccagg                    50

<210> SEQ ID NO 5
<211> LENGTH: 50
<212> TYPE: RNA
<213> ORGANISM: Artificial
<220> FEATURE:
<221> NAME/KEY: misc_feature
<222> LOCATION: (1)..(50)
<223> OTHER INFORMATION: aptamer that binds to glutamate receptor, AMPA
      subtype

<400> SEQUENCE: 5
agaagcaagc gggcacguua cuuauguaac uauacgugua gugcguucgg                    50

<210> SEQ ID NO 6
<211> LENGTH: 49
<212> TYPE: RNA
<213> ORGANISM: Artificial
<220> FEATURE:
<221> NAME/KEY: misc_feature
<222> LOCATION: (1)..(49)
<223> OTHER INFORMATION: aptamer that binds to glutamate receptor, AMPA
      subtype
```

-continued

```
<400> SEQUENCE: 6
acaacccgcg gagcacgagu gaugcuucaa aggcucccac caaagcaga              49

<210> SEQ ID NO 7
<211> LENGTH: 50
<212> TYPE: RNA
<213> ORGANISM: Artificial
<220> FEATURE:
<221> NAME/KEY: misc_feature
<222> LOCATION: (1)..(50)
<223> OTHER INFORMATION: aptamer that binds to glutamate receptor, AMPA
      subtype

<400> SEQUENCE: 7
uucggcgaug guuacgaugg aauagucgua acuguuccaa aagcgacaga             50

<210> SEQ ID NO 8
<211> LENGTH: 50
<212> TYPE: RNA
<213> ORGANISM: Artificial
<220> FEATURE:
<221> NAME/KEY: misc_feature
<222> LOCATION: (1)..(50)
<223> OTHER INFORMATION: constant regions of aptamer that binds to
      glutamate receptor, AMPA subtype

<400> SEQUENCE: 8
gggagaauuc aacugccauc uaggcaguac uacaagcuuc uggacucggu             50

<210> SEQ ID NO 9
<211> LENGTH: 52
<212> TYPE: RNA
<213> ORGANISM: Artificial
<220> FEATURE:
<221> NAME/KEY: misc_feature
<222> LOCATION: (1)..(52)
<223> OTHER INFORMATION: aptamer that binds to glutamate receptor, AMPA
      subtype

<400> SEQUENCE: 9
gagauuguga agcguaggcu cgaguuuguc ccgcgagcc aaagauuccag ac          52

<210> SEQ ID NO 10
<211> LENGTH: 54
<212> TYPE: RNA
<213> ORGANISM: Artificial
<220> FEATURE:
<221> NAME/KEY: misc_feature
<222> LOCATION: (1)..(54)
<223> OTHER INFORMATION: aptamer that binds to glutamate receptor, AMPA
      subtype

<400> SEQUENCE: 10
ggagauugug aagcguaggc ucgaguuugu cccgcgagcc aaagauucca gacc        54

<210> SEQ ID NO 11
<211> LENGTH: 56
<212> TYPE: RNA
<213> ORGANISM: Artificial
<220> FEATURE:
<221> NAME/KEY: misc_feature
<222> LOCATION: (1)..(56)
<223> OTHER INFORMATION: aptamer that binds to glutamate receptor, AMPA
      subtype

<400> SEQUENCE: 11
gggagauugu gaagcguagg cucgaguuug ucccgcgagc caaagauucc agaccc      56
```

```
<210> SEQ ID NO 12
<211> LENGTH: 58
<212> TYPE: RNA
<213> ORGANISM: Artificial
<220> FEATURE:
<221> NAME/KEY: misc_feature
<222> LOCATION: (1)..(58)
<223> OTHER INFORMATION: aptamer that binds to glutamate receptor, AMPA
      subtype

<400> SEQUENCE: 12 gggagauug ugaagcguag gcucgaguuu gucccgcgag ccaaagauuc cagacccc          58

<210> SEQ ID NO 13
<211> LENGTH: 60
<212> TYPE: RNA
<213> ORGANISM: Artificial
<220> FEATURE:
<221> NAME/KEY: misc_feature
<222> LOCATION: (1)..(60)
<223> OTHER INFORMATION: aptamer that binds to glutamate receptor, AMPA
      subtype

<400> SEQUENCE: 13
gggggagauu gugaagcgua ggcucgaguu ugucccgcga gccaaagauu ccagaccccc       60

<210> SEQ ID NO 14
<211> LENGTH: 100
<212> TYPE: RNA
<213> ORGANISM: Artificial
<220> FEATURE:
<221> NAME/KEY: misc_feature
<222> LOCATION: (1)..(100)
<223> OTHER INFORMATION: aptamer that binds to glutamate receptor, AMPA
      subtype

<400> SEQUENCE: 14
gggagaauuc aacugccauc uaggcagauu gugaagcgua ggcucgaguu ugucccgcga       60
gccaaagauu ccagaaguac uacaagcuuc uggacucggu                           100

<210> SEQ ID NO 15
<211> LENGTH: 45
<212> TYPE: RNA
<213> ORGANISM: Artificial
<220> FEATURE:
<221> NAME/KEY: misc_feature
<222> LOCATION: (1)..(45)
<223> OTHER INFORMATION: aptamer that binds to glutamate receptor, AMPA
      subtype

<400> SEQUENCE: 15
gguucaacug ccaucuaggc agauugugaa gcguaggcuc gagcc                      45

<210> SEQ ID NO 16
<211> LENGTH: 46
<212> TYPE: RNA
<213> ORGANISM: Artificial
<220> FEATURE:
<221> NAME/KEY: misc_feature
<222> LOCATION: (1)..(46)
<223> OTHER INFORMATION: aptamer that binds to glutamate receptor, AMPA
      subtype

<400> SEQUENCE: 16
ggagaaucaa cugccaucua ggcagaagcg uaggcucgau uugucc                     46
```

```
<210> SEQ ID NO 17
<211> LENGTH: 48
<212> TYPE: RNA
<213> ORGANISM: Artificial
<220> FEATURE:
<221> NAME/KEY: misc_feature
<222> LOCATION: (1)..(48)
<223> OTHER INFORMATION: aptamer that binds to glutamate receptor, AMPA
      subtype

<400> SEQUENCE: 17
ggagaaucaa cucaucuaga gauugugaag cguaggcucg auuugucc                    48
```